(12) United States Patent
Mizuno et al.

(10) Patent No.: US 11,015,987 B2
(45) Date of Patent: May 25, 2021

(54) TEMPERATURE ESTIMATION METHOD

(71) Applicant: Mitsubishi Electric Corporation, Chiyoda-ku (JP)

(72) Inventors: Kota Mizuno, Chiyoda-ku (JP); Satoru Toyama, Chiyoda-ku (JP); Ryuichi Nishiura, Chiyoda-ku (JP); Tsuyoshi Amimoto, Chiyoda-ku (JP); Ryota Kuriyama, Chiyoda-ku (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 304 days.

(21) Appl. No.: 16/094,760

(22) PCT Filed: Jun. 6, 2017

(86) PCT No.: PCT/JP2017/020925
§ 371 (c)(1),
(2) Date: Oct. 18, 2018

(87) PCT Pub. No.: WO2017/213116
PCT Pub. Date: Dec. 14, 2017

(65) Prior Publication Data
US 2019/0128749 A1    May 2, 2019

(30) Foreign Application Priority Data
Jun. 7, 2016    (JP) .............................. JP2016-113580

(51) Int. Cl.
*G01N 33/28* (2006.01)
*G01K 11/00* (2006.01)
(Continued)

(52) U.S. Cl.
CPC ............. *G01K 11/00* (2013.01); *G01N 33/28* (2013.01); *G01N 33/2835* (2013.01);
(Continued)

(58) Field of Classification Search
CPC ........... G01N 33/2841; G01N 21/3504; G01N 33/28; G01N 33/2835; G01N 33/2888;
(Continued)

(56) References Cited

U.S. PATENT DOCUMENTS

| | | | | |
|---|---|---|---|---|
| 3,027,086 A | * | 3/1962 | Hargens | G06F 3/09 |
| | | | | 702/23 |
| 4,469,661 A | * | 9/1984 | Shultz | A62D 3/32 |
| | | | | 423/210.5 |

(Continued)

FOREIGN PATENT DOCUMENTS

| | | | |
|---|---|---|---|
| CN | 103149120 A | * | 6/2013 |
| CN | 104597202 A | * | 5/2015 |

(Continued)

OTHER PUBLICATIONS

International Search Report dated Aug. 29, 2017, in PCT/JP2017/020925 filed Jun. 6, 2017.

(Continued)

*Primary Examiner* — Gail Kaplan Verbitsky
(74) *Attorney, Agent, or Firm* — Xsensus LLP

(57) ABSTRACT

A temperature estimation method estimating a temperature of a heat generating site in an oil-immersed electric appliance immersed in insulating oil, the insulating oil being silicone oil or ester oil. The temperature estimation method includes measuring concentrations of two types of thermal decomposition products in the insulating oil and calculating a temperature of the heat generating site in the oil-immersed electric appliance based on a concentration ratio between the two types of thermal decomposition products and a relational expression between the temperature of the heat generating site and the concentration ratio prepared in advance. When the silicone oil is adopted as the insulating oil, at least one of the two types of thermal decomposition products is straight-chain siloxane, alcohol containing silicon, or ben- (Continued)

zene. When the ester oil is adopted as the insulating oil, the two types of thermal decomposition products are fatty acids.

11 Claims, 15 Drawing Sheets

(51) Int. Cl.
*H01F 41/00* (2006.01)
*H01F 27/32* (2006.01)

(52) U.S. Cl.
CPC ......... *H01F 41/00* (2013.01); *G01N 33/2841* (2013.01); *H01F 27/321* (2013.01)

(58) Field of Classification Search
CPC ........ H01F 27/00; H01F 27/324; H01F 27/12; H01F 27/402; H01F 27/34; H01F 27/321; H01F 27/32; H01F 5/06; G01K 11/00
See application file for complete search history.

(56) References Cited

U.S. PATENT DOCUMENTS

| | | | | |
|---|---|---|---|---|
| 5,659,126 | A * | 8/1997 | Farber | G01N 1/26 422/80 |
| 9,419,430 | B1 * | 8/2016 | Tostrud | H02H 6/005 |
| 9,599,653 | B2 * | 3/2017 | Kim | G01N 33/0004 |
| 10,214,703 | B2 * | 2/2019 | Fletcher | C10M 135/10 |
| 10,359,411 | B2 * | 7/2019 | Kuriyama | H01F 27/00 |
| 10,761,079 | B2 * | 9/2020 | Kuriyama | G01N 21/3504 |
| 2013/0134367 | A1 * | 5/2013 | Kato | G01N 33/287 252/570 |
| 2014/0274840 | A1 * | 9/2014 | Esche | C10M 159/18 508/362 |
| 2019/0277805 | A1 * | 9/2019 | Wrobel | G01H 15/00 |
| 2019/0383731 | A1 * | 12/2019 | Brauer | G01N 21/3504 |
| 2020/0013535 | A1 * | 1/2020 | Yamaguchi | H01B 3/46 |
| 2020/0326364 | A1 * | 10/2020 | Okazaki | H01B 3/52 |
| 2020/0333317 | A1 * | 10/2020 | Virtanen | G01N 33/0059 |
| 2021/0033570 | A1 * | 2/2021 | Kato | H01F 27/00 |

FOREIGN PATENT DOCUMENTS

| | | | | |
|---|---|---|---|---|
| JP | 5-249100 | A | | 9/1993 |
| JP | 2004-200348 | A | | 7/2004 |
| JP | 2013-131511 | A | | 7/2013 |
| JP | 6045766 | B1 * | 12/2016 | ......... G01N 33/2841 |
| KR | 848137 | B1 * | 7/2008 | |
| KR | 101290807 | B1 * | 7/2013 | |

OTHER PUBLICATIONS

Wang, Z. et al., "Gas Generation in Natural Ester and Mineral Oil Under Partial Discharge and Sparking Faults", IEEE Electrical Insulation Magazine, vol. 29, No. 5, 2013, pp. 62-70.
Denki Kyodo Kenkyu, Aburairi Hen-atsuki no Hoshu Kanri, Electric Technology Research Association, vol. 54, No. 5 (1), 1999, 27 pages.

* cited by examiner

TEMPERATURE ESTIMATION METHOD

TECHNICAL FIELD

The present invention relates to a method of estimating a temperature of a heat generating site in an oil-immersed electric appliance.

BACKGROUND ART

A method of diagnosing an abnormal condition such as overheat abnormality of an oil-immersed electric appliance such as a transformer without turning off the appliance with a type or a concentration of a gas component in insulating oil or a concentration ratio between a plurality of gas components being defined as an indicator has been known (for example, NPD 1 (Z. Wang, X. Wang, X. Yi and S. Li, "Gas Generation in Natural Ester and Mineral Oil Under Partial Discharge and Sparking Faults," IEEE Electrical Insulation Magazine, Vol. 29, No. 5, pp. 62-70, 2013) and NPD 2 (Denki Kyodo Kenkyu, Vol. 54, No. 5 (1), Aburairi Hen-atsuki no Hoshu Kanri, Electric Technology Research Association, February 1999)). Many works associated with such an abnormal condition diagnosis method for an oil-immersed transformer in which mineral oil is employed as insulating oil through analysis of gas in oil have been built up and guidelines for diagnosis of an abnormal condition have also been proposed domestically and abroad.

In a vehicle-mounted oil-immersed electric appliance (such as a transformer) for rail vehicles, with safety being focused on, silicone oil higher in flash point and higher in safety than mineral oil is sometimes employed as insulating oil (an insulating medium also serving as a cooling medium). In recent years, ester oil which is excellent not only in safety but also in biodegradability and low in environmental loads has increasingly been applied (for example, PTD 1 (Japanese Patent Laying-Open No. 2013-131511)).

Non-mineral oil such as silicone oil or ester oil is different in composition from mineral oil. The non-mineral oil is different from mineral oil in type and concentration of gas components generated at the time of occurrence of such an abnormal condition as discharge abnormality and abnormal overheat and in concentration ratio between a plurality of gas components. Therefore, a method of diagnosing an oil-immersed electric appliance in which mineral oil is used cannot be applied as it is to diagnosis of an abnormal condition of an oil-immersed electric appliance in which silicone oil is used.

PTD 2 (Japanese Patent Laying-Open No. 5-249100) discloses a method of determining degradation of an oil-immersed electric appliance in which synthetic oil such as silicone oil is used. In PTD 2, oil sampled from the oil-immersed electric appliance is analyzed with an analysis instrument such as a gas chromatograph to detect trimeric to hexameric cyclic siloxanes representing thermal decomposition products specific to silicone oil. A temperature of a heat generating site in the oil-immersed electric appliance is then determined based on a ratio of concentration of such cyclic siloxane in oil.

CITATION LIST

Patent Document

PTD 1: Japanese Patent Laying-Open No. 2013-131511
PTD 2: Japanese Patent Laying-Open No. 5-249100

Non Patent Document

NPD 1: Z. Wang, X. Wang, X. Yi and S. Li, "Gas Generation in Natural Ester and Mineral Oil Under Partial Discharge and Sparking Faults," IEEE Electrical Insulation Magazine, Vol. 29, No. 5, pp. 62-70, 2013
NPD 2: Denki Kyodo Kenkyu, Vol. 54, No. 5 (1), Aburairi Hen-atsuki no Hoshu Kanri, Electric Technology Research Association, February 1999

SUMMARY OF INVENTION

Technical Problem

As a result of studies conducted by the present inventors, however, it has been found that a behavior in thermal decomposition of silicone oil is different between a temperature region from 100° C. to 700° C. and a temperature region not lower than 700° C. Specifically, a ratio of concentration of trimeric cyclic siloxane to hexameric cyclic siloxane in oil is higher as a heating temperature is higher in a range from 100° C. to 700° C., whereas the ratio tends to stop increasing at the time point when the heating temperature exceeds 700° C. (see Comparative Example 1 and FIG. 3).

Therefore, with the degradation determination method in PTD 2, when abnormal overheat exceeding 700° C. occurs, a temperature cannot accurately be measured and diagnosis may be incorrect. Since there is currently no technique available for estimating an abnormal overheat temperature of a transformer immersed in ester oil, a method of diagnosing an abnormal condition of a transformer immersed in ester oil should immediately be developed.

The present invention was made in view of the problems above, and an object thereof is to provide a temperature estimation method capable of highly accurately estimating a temperature of a heat generating site in an oil-immersed electric appliance immersed in silicone oil or an oil-immersed electric appliance immersed in ester oil.

Solution to Problem

The temperature estimation method in the present invention is a method of estimating a temperature of a heat generating site in an oil-immersed electric appliance immersed in insulating oil, the insulating oil being silicone oil or ester oil (an oil-immersed electric appliance immersed in silicone oil or an oil-immersed electric appliance immersed in ester oil).

The method of estimating a temperature of the oil-immersed electric appliance immersed in the silicone oil includes a measurement step of measuring concentrations of two types of thermal decomposition products in the silicone oil and a calculation step of calculating a temperature of the heat generating site in the oil-immersed electric appliance based on a concentration ratio between the two types of thermal decomposition products and a relational expression between the temperature of the heat generating site and the concentration ratio prepared in advance.

At least one of the two types of thermal decomposition products is straight-chain siloxane, alcohol containing silicon, or benzene.

The method of estimating a temperature of the oil-immersed electric appliance immersed in the ester oil includes a measurement step of measuring concentrations of two types of thermal decomposition products in the ester oil and a calculation step of calculating a temperature of the heat generating site in the oil-immersed electric appliance based on a concentration ratio between the two types of thermal decomposition products and a relational expression between the temperature of the heat generating site and the concentration ratio prepared in advance.

The two types of thermal decomposition products are fatty acids.

Advantageous Effects of Invention

According to the present invention, a temperature estimation method capable of highly accurately estimating a temperature of a heat generating site in an oil-immersed electric appliance immersed in silicone oil or an oil-immersed electric appliance immersed in ester oil can be provided.

DESCRIPTION OF EMBODIMENTS

One embodiment of the present invention will be described below.

First Embodiment

The temperature estimation method in the present invention is a method of estimating a temperature of a site of heat generation (due to occurrence of abnormal overheat in a part of an oil-immersed electric appliance) in an oil-immersed electric appliance immersed in silicone oil.

Examples of the oil-immersed electric appliance include an oil-immersed electric appliance in which coil copper wrapped with coil insulating paper is arranged in silicone oil, and specifically include a transformer. Since silicone oil is often used in a vehicle-mounted oil-immersed electric appliance (for rail vehicles) with safety being focused on, the temperature estimation method in the present embodiment can suitably be used for a vehicle-mounted oil-immersed electric appliance.

Silicone oil is composed of silicone which exhibits properties of oil (a polymeric compound having a main skeleton attributed to siloxane bonds). Dimethylpolysiloxane is most representative of silicone oil, without particularly being limited thereto. A part of a side chain (a methyl group) of dimethylpolysiloxane may be substituted with hydrogen or a phenyl group.

The temperature estimation method in the present embodiment includes a sampling step, a measurement step, and a calculation step.

Figure 1:
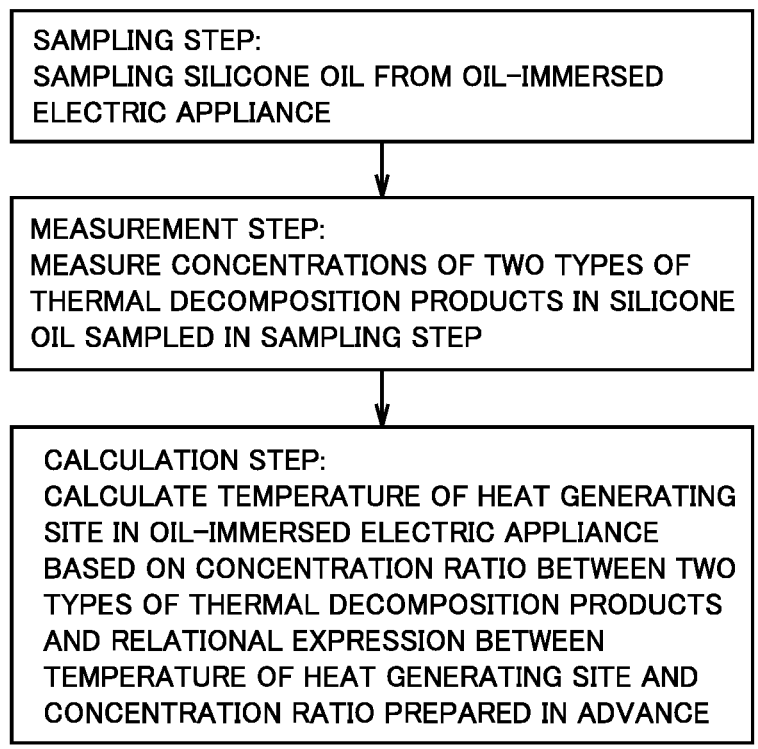
FIG. 1 is a flowchart of a temperature estimation method in the present embodiment.

FIG. 1 is a flowchart of the temperature estimation method in the present embodiment. Details of each step will be described below with reference to FIG. 1.

(Sampling Step)

In the sampling step, silicone oil is sampled from the oil-immersed electric appliance.

In order to perform the temperature estimation method in the present embodiment, initially, silicone oil is sampled from an oil drain valve of the oil-immersed electric appliance to a glass container or a polyethylene container. Since silicone oil circulates through the inside of the electric appliance, a thermal decomposition product of silicone oil is distributed in the appliance at a substantially uniform concentration. Though an amount of insulating oil actually used for analysis is approximately 0.1 mL, 10 mL to 100 mL of oil is preferably sampled in consideration of introduction of a foreign matter from the outside.

(Measurement Step)

In the measurement step, concentrations of two types of thermal decomposition products (compounds generated as a result of thermal decomposition of components in silicone oil) in the silicone oil sampled in the sampling step are measured.

Measurement can be conducted, for example, with such an analysis instrument as a gas chromatograph mass spectrometer (GC/MS). An analysis method should only be able to analyze thermal decomposition products of the silicone oil, and another column, another analysis condition, or another analyzer adapted to a gas chromatograph or the like incorporating an FID detector may be employed.

Before the sampled silicone oil is subjected to analysis, a standard solution in which each thermal decomposition product has been dissolved at an already known concentration is also subjected to measurement in advance, and based on a measurement value therefrom, a calibration curve is prepared. With the calibration curve, a concentration of a thermal decomposition product contained in the sampled silicone oil can be calculated.

In the present embodiment, at least one of two types of detected thermal decomposition products is straight-chain siloxane, alcohol containing silicon, or benzene.

From a point of view of sensitivity in analysis, straight-chain siloxane is preferably dimeric hexamethyldisiloxane (M2) or trimeric octamethyltrisiloxane (M3), however, it may be tetrameric or higher straight-chain siloxane.

From a point of view of sensitivity in analysis, alcohol containing silicon is preferably trimethylsilanol, however, silanol containing no carbon or alcohol containing silicon and two or more carbon atoms may be applicable.

One of the two types of thermal decomposition products may be a thermal decomposition product other than the compounds above (straight-chain siloxane, alcohol containing silicon, and benzene). Examples of such a thermal decomposition compound include cyclic siloxane.

From a point of view of sensitivity in analysis, cyclic siloxane is preferably trimeric hexamethylcyclotrisiloxane (D3), tetrameric octamethylcyclotetrasiloxane (D4), or pentameric decamethylcyclopentasiloxane (D5), however, heptameric or higher straight-chain siloxane may be applicable.

(Calculation Step)

In the calculation step, a temperature of the heat generating site in the oil-immersed electric appliance is calculated based on a concentration ratio between two types of thermal decomposition products and a relational expression between the temperature of the heat generating site and the concentration ratio prepared in advance.

Initially, before the calculation step, Test Example 1 (a heating test) which will be described later is performed in advance and a relational expression between a temperature of the heat generating site and a concentration ratio (a calibration curve) is prepared as in Examples.

Then, a concentration ratio is calculated based on measurement values of concentrations of the two types of thermal decomposition products. A temperature of the heat generating site in the oil-immersed electric appliance can be calculated from the concentration ratio based on the relational expression between the temperature of the heat generating site and the concentration ratio prepared in advance.

A concentration ratio preferably of hexamethylcyclotrisiloxane (D3)/trimethylsilanol, hexamethylcyclotrisiloxane (D3)/benzene, octamethylcyclotetrasiloxane (D4)/trimethylsilanol, benzene/octamethylcyclotetrasiloxane (D4), octamethyltrisiloxane (M3)/hexamethyldisiloxane (M2), or benzene/trimethylsilanol serves as an indicator in estimation of a temperature.

Examples of the concentration ratio serving as the indicator in estimation of a temperature other than the above include concentration ratios of octamethyltrisiloxane (M3)/hexamethylcyclotrisiloxane (D3), M3/octamethylcyclotetrasiloxane (D4), hexamethyldisiloxane (M2)/trimethylsilanol, M3/trimethylsilanol, and M3/trimethylsilanol.

It has been confirmed in the studies conducted by the present inventors that these concentration ratios highly correlate with a temperature of the heat generating site in a wide temperature range (in particular in a high-temperature region) (see Examples). A temperature of the heat generating site in the oil-immersed electric appliance immersed in silicone oil can highly accurately be estimated by using these concentration ratios.

In the measurement step, two types of thermal decomposition products corresponding to these combinations of concentration ratios are subjected to measurement.

A concentration of a thermal decomposition product generated as a result of occurrence of abnormal overheat in the oil-immersed electric appliance is different depending on a duration of abnormal overheat and an area (a volume) of the heat generating site other than the temperature of the heat generating site, and it is difficult to estimate a temperature of the heat generating site (a temperature of abnormal overheat) with only a concentration of a thermal decomposition product being used as the indicator.

A concentration ratio between two types of thermal decomposition products in silicone oil, however, is dependent on a temperature of the heat generating site, not on a duration of abnormal overheat or an area of the heat generating site. Since an amount of insulating oil (silicone oil) is sufficiently greater than an amount of generation of a thermal decomposition product and close to indefinite supply, the thermal decomposition product is kept generated at a constant rate at a certain temperature and a concentration ratio between two types of thermal decomposition products is constant. Therefore, the concentration ratio between two types of thermal decomposition products can be considered as dependent only on a temperature, not on time or an area. This is considered as similarly applicable also to analysis of gas components in insulating oil in maintenance of an oil-immersed transformer (see Electric Technology Research Association, "Denki Kyodo Kenkyu," Vol. 54, No. 5 (1), page 33, right column, lowermost paragraph, section (katakana character "i")).

Therefore, a temperature of abnormal overheat can be estimated by using a concentration ratio between two types of thermal decomposition products in the present embodiment.

Though a method with the use of two types of thermal decomposition products as the indicator is described in the present embodiment, yet another indicator may also be added for estimation of a temperature of the heat generating site for the purpose of improving estimation accuracy.

When an estimated temperature value obtained with the temperature estimation method exceeds a statistically or empirically predetermined threshold temperature, measures for preventing occurrence of an internal abnormal condition can be taken by stopping an operation of the oil-immersed electric appliance. By thus using the temperature estimation method in the present embodiment, an internal abnormal condition (a failure) of an oil-immersed electric appliance can be predicted and precautionary maintenance of the oil-immersed electric appliance can be done.

In the present embodiment, an internal abnormal condition of an oil-immersed electric appliance can be predicted and precautionary maintenance of the oil-immersed electric appliance can be done without turning off the appliance for internal inspection each time of periodic check.

Test Example 1

In Test Example 1, concentrations of a plurality of thermal decomposition products at each temperature were measured in a test system (see FIG. 12) which simulated occurrence of abnormal overheat in an oil-immersed electric appliance immersed in silicone oil. Relation between a concentration ratio between two thermal decomposition products and a heating temperature was analyzed based on measurement values in Examples and Comparative Examples which will be described later.

Seven types of thermal decomposition products of hexamethylcyclotrisiloxane (D3), octamethylcyclotetrasiloxane (D4), decamethylcyclopentasiloxane (D5), hexamethyldisiloxane (M2), octamethyltrisiloxane (M3), trimethylsilanol, and benzene were subjected to measurement.

Figure 12:
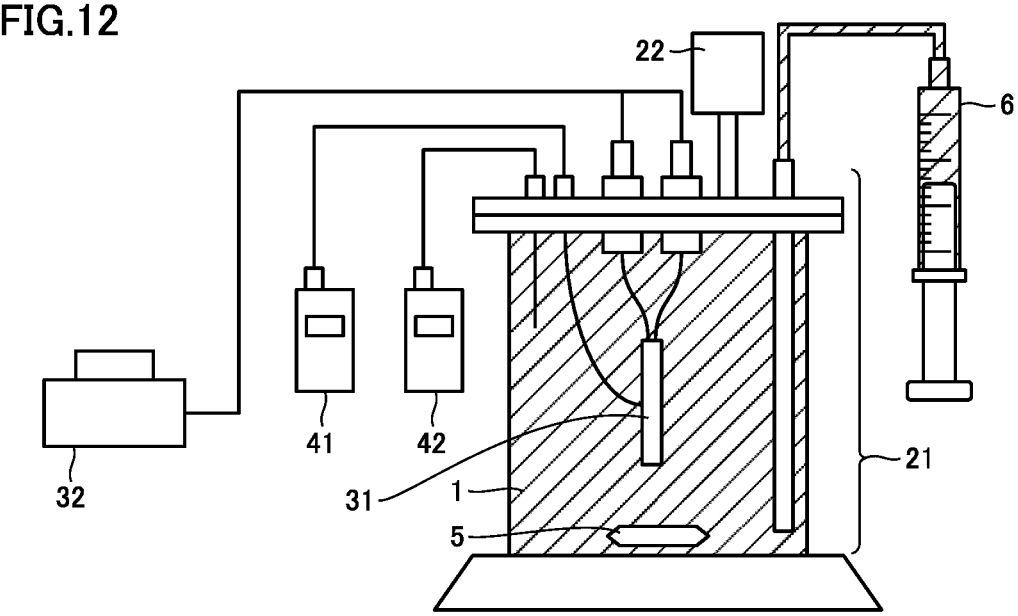
FIG. 12 is a schematic diagram of a test system simulating occurrence of abnormal overheat in an oil-immersed electric appliance in Test Example 1.

Referring to FIG. 12, in order to simulate occurrence of abnormal overheat in an oil-immersed electric appliance immersed in silicone oil, a heater 31 was set in a test vessel 21 and silicone oil 1 was heated. KF-96-50cs manufactured by Shin-Etsu Chemical Co., Ltd. was employed as silicone oil 1. Test vessel 21 was provided with a conservator 22 and heater 31 was powered by an AC power supply 32.

Temperatures of heater 31 and silicone oil 1 were measured with a thermometer 41 and a thermometer 42, respectively.

Heating by heater 31 was controlled based on measurement values from thermometers 41 and 42, and a temperature of heater 31 was maintained at 300° C., 400° C., 500° C., 600° C., 700° C., 800° C., and 900° C. In order to uniformly dissolve a thermal decomposition product of the silicone oil, silicone oil 1 was agitated with an agitator 5. After heating for ten minutes at each temperature, silicone oil 1 was sampled with a removable oil sampling syringe 6. Silicone oil 1 (new oil) before heating was also sampled in advance as a control.

Concentrations of the seven types of thermal decomposition products contained in the sampled silicone oil were measured with a gas chromatograph mass spectrometer (GC/MS). Measurement was conducted three times for each silicone oil sampled as above.

Specifically, 0.1 mL of sampled silicone oil was dissolved in 1 mL of hexane, and the solution was directly introduced into the gas chromatograph mass spectrometer with a split method (at a split ratio of 1:10) and analyzed with an HP-5 column (having a length of 30 m×an inner diameter of 0.25 mm×a film thickness of 0.25 µm) of Agilent Technologies.

A temperature at an introduction port was raised in a procedure of "280° C., a column temperature being set to 60° C. (held for five minutes)"→"temperature increase (5° C./minute)"→"highest temperature at 300° C. (held for five minutes)."

A gas chromatograph mass spectrometer was used for identifying an unknown thermal decomposition product. After the thermal decomposition product was known, analysis could also be conducted with an analyzer capable of quantitatively analyzing that compound (for example, a gas chromatograph apparatus incorporating a hydrogen flame ionization detector (FID)).

When standard solutions in which various types of thermal decomposition products had been dissolved in silicone oil at already known concentrations were also subjected to measurement and calibration curves were prepared at the same time, a concentration of a thermal decomposition product contained in the heated silicone oil could be calculated based on the calibration curves.

Figure 2:
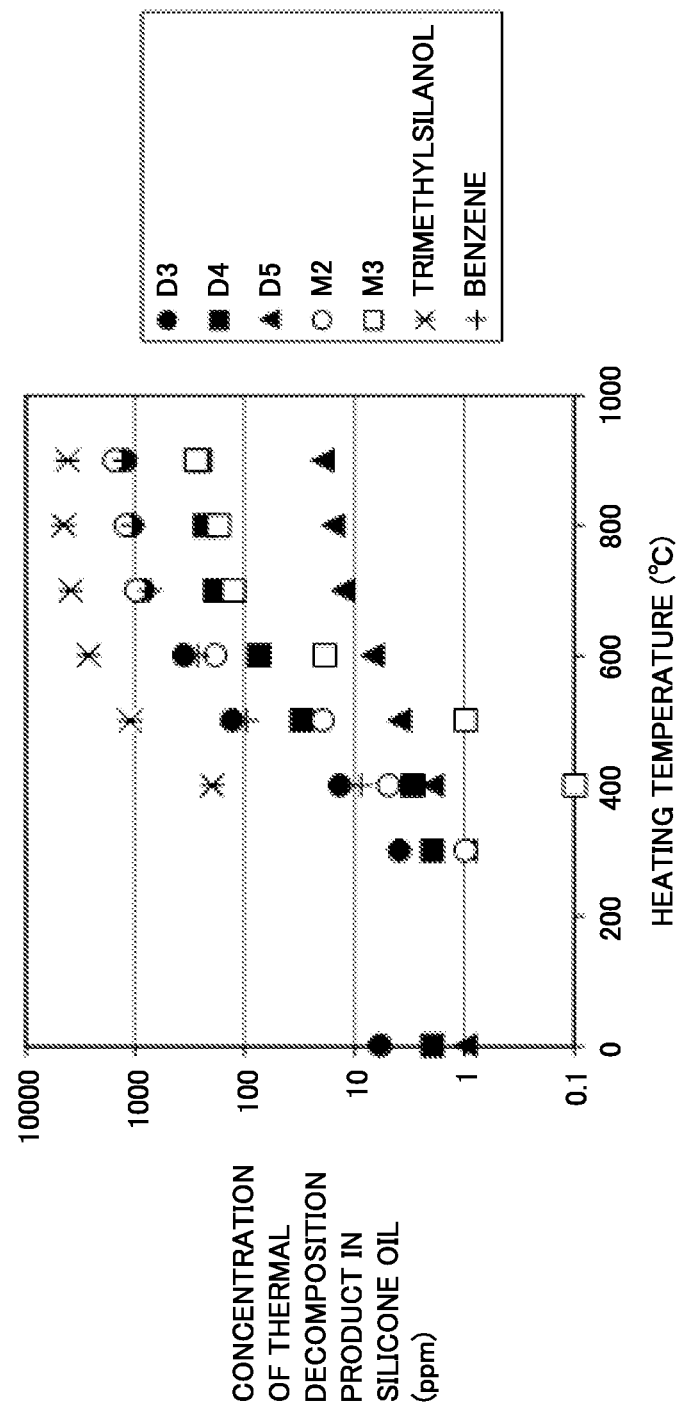
FIG. 2 shows a graph showing results of measurement of a concentration of a thermal decomposition product in Test Example 1.

Table 1 and FIG. 2 show results of measurement of a concentration of each thermal decomposition product at each heating temperature. FIG. 2 shows results of measurement of new oil in a portion where a heating temperature was 0.

TABLE 1

| | | Concentration of Thermal Decomposition Product (unit: ppm) | | | | | | |
|---|---|---|---|---|---|---|---|---|
| | | D3 | D4 | D5 | M2 | M3 | Trimethyl-silanol | Benzene |
| Heating Temperature | New Oil | 6 | 2 | 1 | 0 | 0 | 0 | 0 |
| | 300° C. | 4 | 2 | 1 | 1 | 0 | 0 | 2 |
| | 400° C. | 14 | 3 | 2 | 5 | 0.1 | 203 | 9 |
| | 500° C. | 134 | 31 | 4 | 20 | 1 | 1135 | 98 |
| | 600° C. | 368 | 76 | 7 | 191 | 19 | 2728 | 274 |
| | 700° C. | 860 | 192 | 13 | 1006 | 130 | 3963 | 748 |
| | 800° C. | 1106 | 237 | 16 | 1253 | 179 | 4583 | 1075 |
| | 900° C. | 1264 | 262 | 20 | 1591 | 284 | 4247 | 1298 |

As shown in Table 1 and FIG. 2, a concentration in oil increases as a heating temperature is higher in all of the seven types of thermal decomposition products subjected to measurement (D3, D4, D5, M2, M3, trimethylsilanol, and benzene).

As described above, in order to estimate a temperature of the heat generating site in the oil-immersed electric appliance immersed in silicone oil, a concentration ratio between two types of thermal decomposition products is effectively used as the indicator. In Comparative Examples and Examples which will be described next, measurement results in Table 1 were used to calculate concentration ratios between two types of thermal decomposition products in various combinations and to analyze relation between the concentration ratio and a heating temperature.

Comparative Example 1

Figure 3:
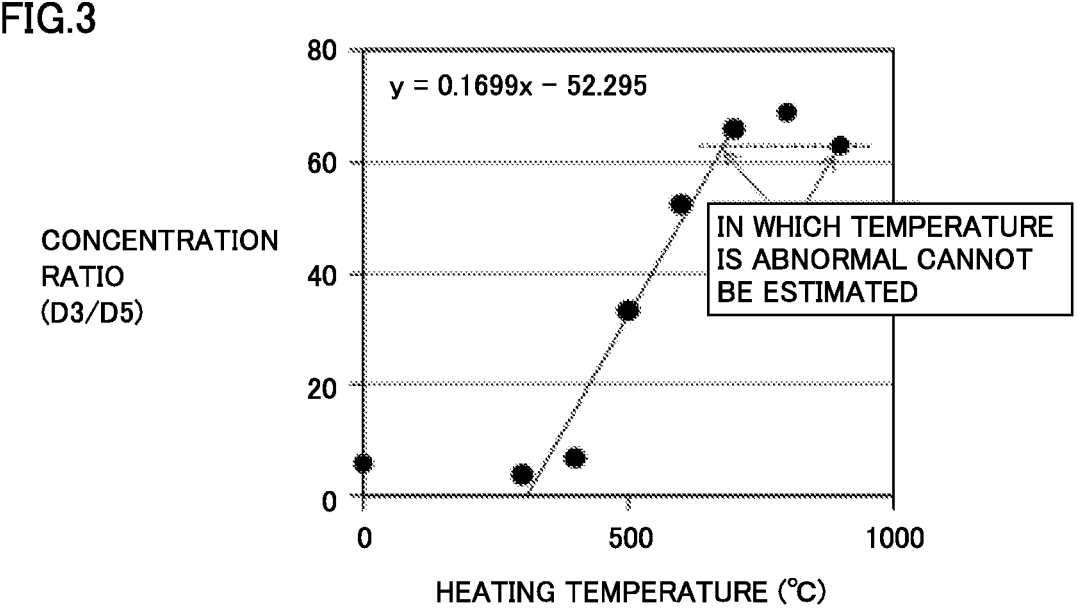
FIG. 3 shows a graph showing relation between a concentration ratio between thermal decomposition products (D3/D5) and a heating temperature in Comparative Example 1.

FIG. 3 shows a graph showing relation between a concentration ratio between thermal decomposition products (D3/D5) and a heating temperature in Comparative Example 1. A concentration ratio shown in FIG. 3 represents a concentration ratio between only cyclic siloxanes (D3 and D5) as in the method disclosed in PTD 2.

The figure shows a plot of a concentration ratio at each heating temperature, a regression line found from the plots with a least square method, and a relational expression (a regression expression) thereof, which is also applicable to figures that follow.

The relational expression (calibration curve) was prepared not by using a temperature of silicone oil but by using a heating temperature representing a temperature of heater 31 (a value measured with thermometer 41) which simulated a heat generating site. A temperature of the heat generating site in the oil-immersed electric appliance can thus be estimated based on the prepared calibration curve.

Even though heat generation such as abnormal overheat occurs in a part (a local part) of an oil-immersed electric appliance such as an actual transformer, a temperature of the insulating oil (silicone oil 1) itself hardly increases from a temperature in a normal operation (around 100° C.).

It can be seen in FIG. 3 that, though D3/D5 highly correlates with a heating temperature in a temperature region from 300° C. to 700° C., it does not correlate with a heating temperature in a temperature region exceeding 700° C. and D3/D5 does not increase even when the heating temperature increases.

It has been confirmed in the studies conducted by the present inventors that, similarly to D3/D5, concentration ratios of D4/D5, D5/trimethylsilanol, and D5/benzene do not correlate with a heating temperature either in the high-temperature region.

Therefore, a temperature of the heat generating site in the oil-immersed electric appliance immersed in the silicone oil cannot accurately be estimated based on such a concentration ratio.

Comparative Example 2

Figure 5:
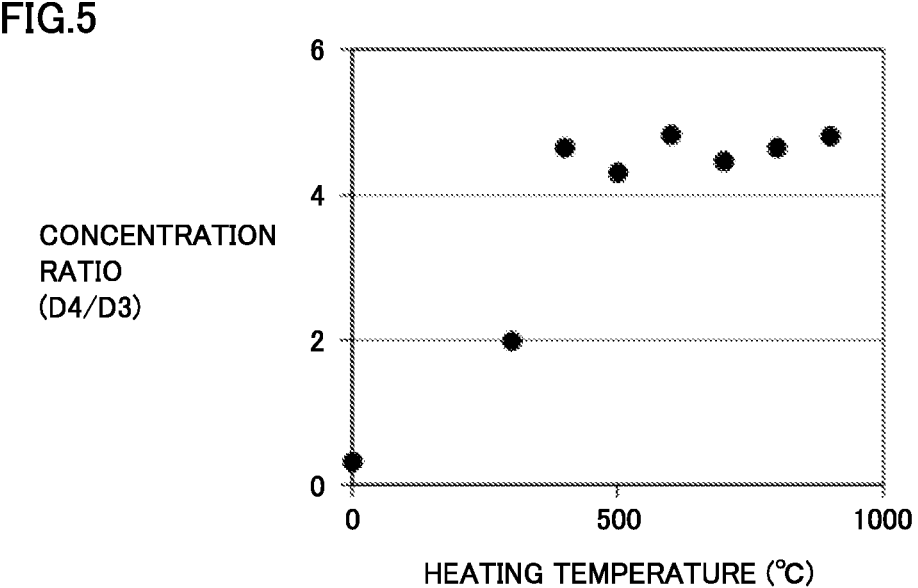
FIG. 5 shows a graph showing relation between a concentration ratio between thermal decomposition products (D4/D3) and a heating temperature in Comparative Example 2.

FIG. 5 shows a graph showing relation between a concentration ratio between thermal decomposition products (D4/D3) and a heating temperature in Comparative Example 2. As shown in FIG. 5, a concentration ratio calculated in connection with a combination of octamethylcyclotetrasiloxane (D4)/hexamethylcyclotrisiloxane (D3) hardly correlated with a heating temperature.

Similarly to D4/D3, low correlation of hexamethyldisiloxane (M2)/hexamethylcyclotrisiloxane (D3), hexamethyldisiloxane (M2)/octamethylcyclotetrasiloxane (D4), hexamethyldisiloxane (M2)/decamethylcyclopentasiloxane (D5), octamethyltrisiloxane (M3)/decamethylcyclopentasiloxane (D5), and hexamethyldisiloxane (M2)/benzene with a heating temperature was also confirmed in the studies conducted by the present inventors.

Therefore, a temperature of the heat generating site in the oil-immersed electric appliance immersed in the silicone oil cannot accurately be estimated based on such a concentration ratio.

Examples 1 to 6

Figure 6:
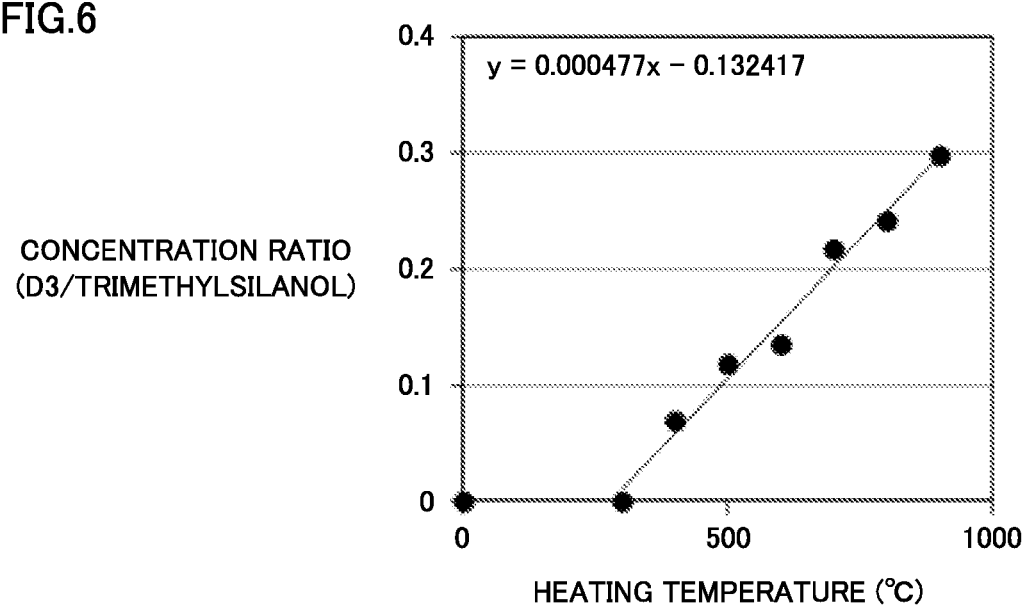
FIG. 6 shows a graph showing relation between a concentration ratio between thermal decomposition products (D3/trimethylsilanol) and a heating temperature in Example 1.

FIG. 6 shows a graph showing relation between a concentration ratio between thermal decomposition products (hexamethylcyclotrisiloxane (D3)/trimethylsilanol) and a heating temperature in Example 1.

Figure 7:
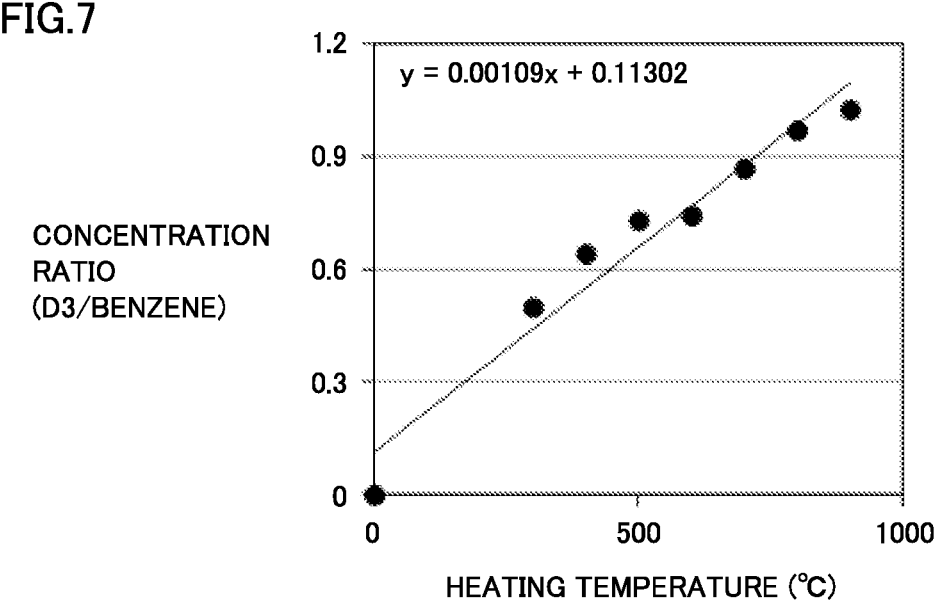
FIG. 7 shows a graph showing relation between a concentration ratio between thermal decomposition products (D3/benzene) and a heating temperature in Example 2.

FIG. 7 shows a graph showing relation between a concentration ratio between thermal decomposition products (hexamethylcyclotrisiloxane (D3)/benzene) and a heating temperature in Example 2.

Figure 8:
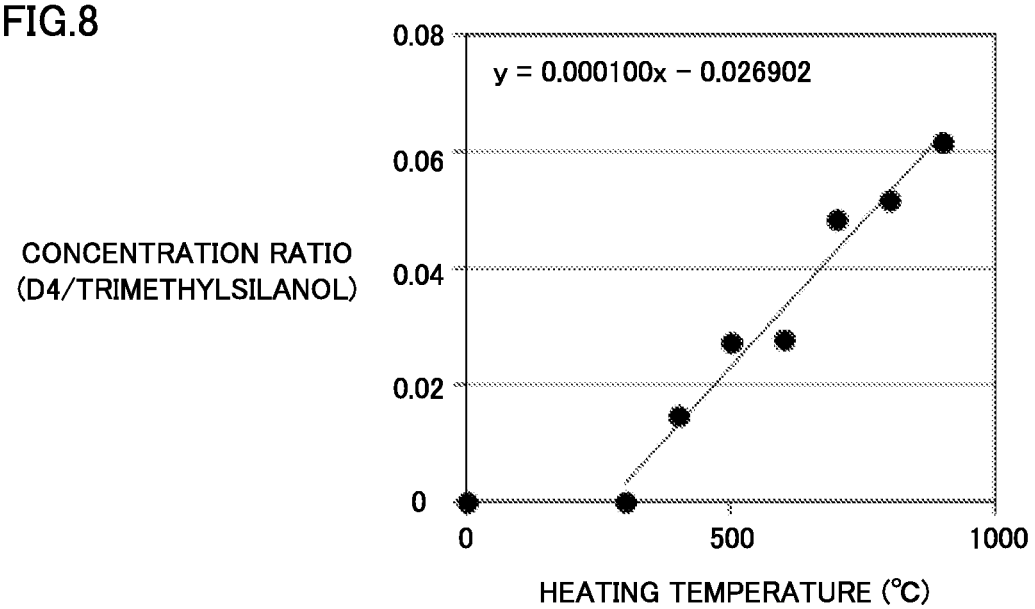
FIG. 8 shows a graph showing relation between a concentration ratio between thermal decomposition products (D4/trimethylsilanol) and a heating temperature in Example 3.

FIG. 8 shows a graph showing relation between a concentration ratio between thermal decomposition products (octamethylcyclotetrasiloxane (D4)/trimethylsilanol) and a heating temperature in Example 3.

Figure 9:
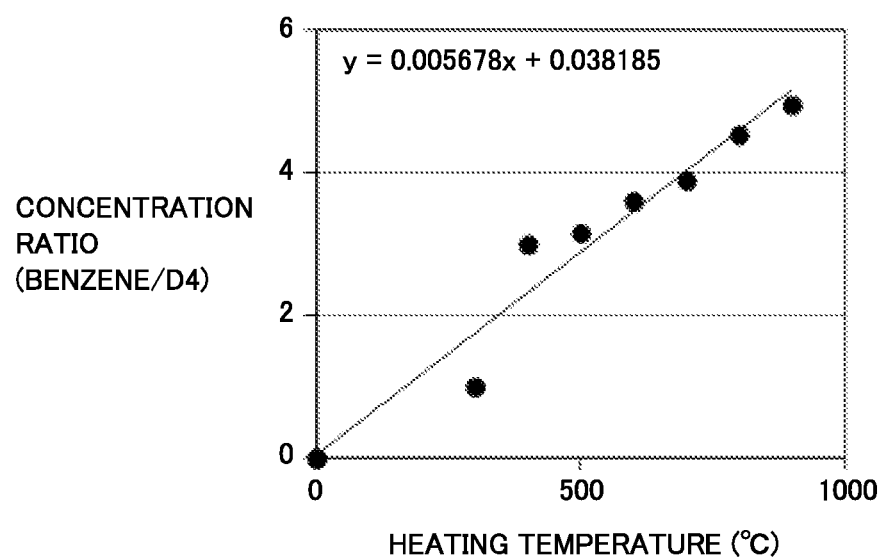
FIG. 9 shows a graph showing relation between a concentration ratio between thermal decomposition products (benzene/D4) and a heating temperature in Example 4.

FIG. 9 shows a graph showing relation between a concentration ratio between thermal decomposition products (benzene/octamethylcyclotetrasiloxane (D4)) and a heating temperature in Example 4.

Figure 10:
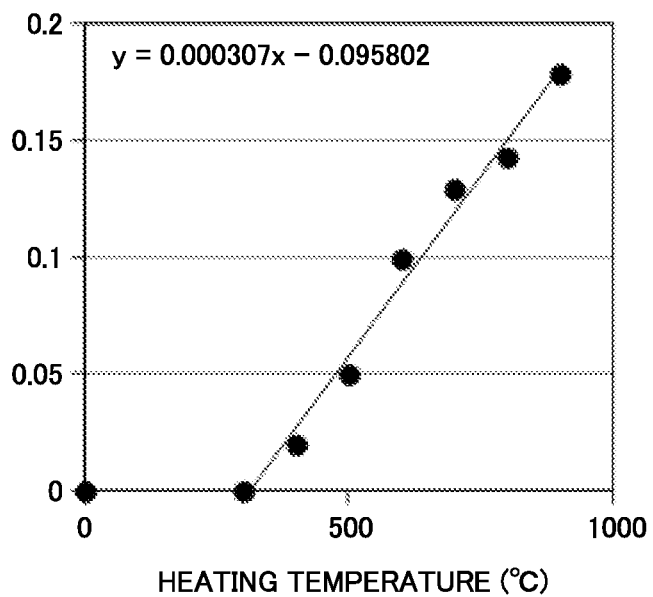
FIG. 10 shows a graph showing relation between a concentration ratio between thermal decomposition products (M3/M2) and a heating temperature in Example 5.

FIG. 10 shows a graph showing relation between a concentration ratio between thermal decomposition products (octamethyltrisiloxane (M3)/hexamethyldisiloxane (M2)) and a heating temperature in Example 5.

Figure 11:
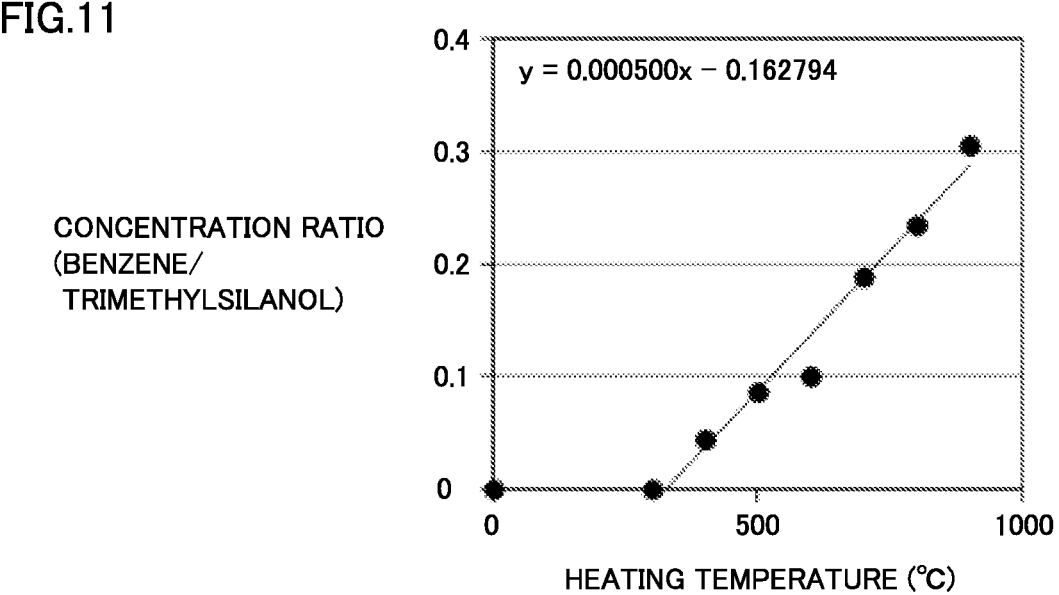
FIG. 11 shows a graph showing relation between a concentration ratio between thermal decomposition products (benzene/trimethylsilanol) and a heating temperature in Example 6.

FIG. 11 shows a graph showing relation between a concentration ratio between thermal decomposition products (benzene/trimethylsilanol) and a heating temperature in Example 6.

It can be seen in the graphs shown in FIGS. 6 to 11 that correlation between the concentration ratios calculated in the combinations in Examples 1 to 6 and heating temperatures is high in a range of heating temperatures from 300° C. to 900° C. Therefore, even when a temperature of the heat generating site in the oil-immersed electric appliance exceeds 700° C., a temperature of the heat generating site can be estimated with the temperature estimation method described in the embodiment with the relational expression shown in FIGS. 6 to 11.

Example 7

Figure 4:
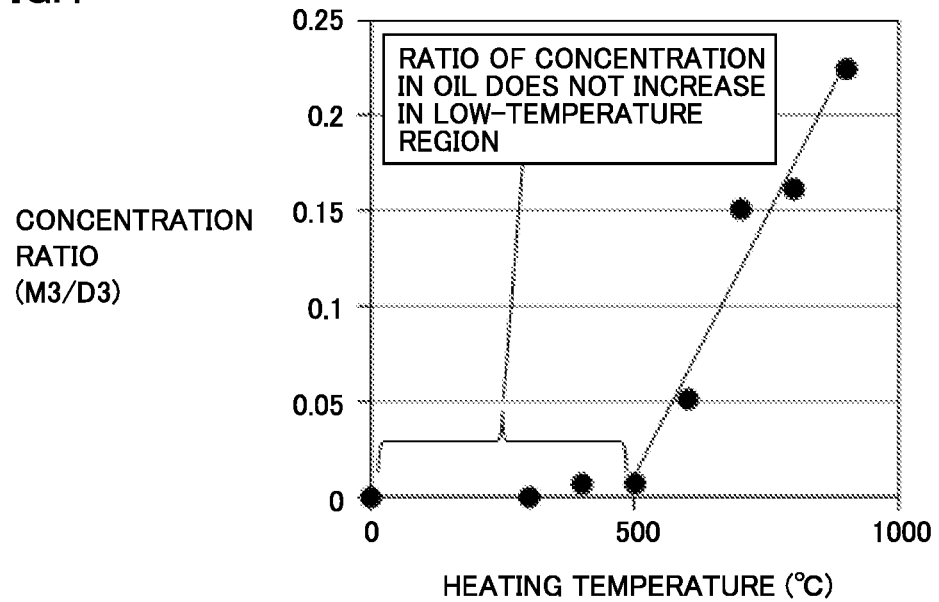
FIG. 4 shows a graph showing relation between a concentration ratio between thermal decomposition products (M3/D3) and a heating temperature in Example 7.

FIG. 4 shows a graph showing relation between a concentration ratio between thermal decomposition products (M3/D3) and a heating temperature in Example 7.

As shown in FIG. 4, octamethyltrisiloxane (M3)/hexamethylcyclotrisiloxane (D3) highly correlates with a heating temperature in a range of heating temperatures from 500° C. to 900° C. Up to a heating temperature of 500° C., however, M3/D3 did not increase.

Similarly to M3/D3, high correlation also of M3/octamethylcyclotetrasiloxane (D4), hexamethyldisiloxane (M2)/trimethylsilanol, M3/trimethylsilanol, and M3/trimethylsilanol with a heating temperature in the high-temperature region and low correlation thereof with a heating temperature in a low-temperature region were also confirmed in the studies conducted by the present inventors.

In using the concentration ratios in these combinations, it is not desirable to estimate a temperature in the low-temperature region (not higher than 500° C.), however, a temperature can be estimated when abnormal overheat occurs in the high-temperature region not lower than a certain temperature (exceeding 500° C.).

Second Embodiment

The temperature estimation method in the present invention is a method of estimating a temperature of a site of heat generation (due to occurrence of abnormal overheat in a part of an oil-immersed electric appliance) in an oil-immersed electric appliance immersed in ester oil.

Examples of the oil-immersed electric appliance include an oil-immersed electric appliance in which coil copper wrapped with coil insulating paper is arranged in ester oil, and specifically include a transformer. Ester oil refers to oil mainly (for example, at least 90 mass %) composed of oil having ester bonds.

Examples of ester oil include polyol ester obtained by esterification between polyalcohol and carboxylic acid and aliphatic ester obtained by esterification between aliphatic carboxylic acid and monoalcohol.

Ester oil is categorized into three types (synthetic ester oil, natural ester oil, and plant-derived ester oil) in Japan and into two types (synthetic ester oil and natural ester oil) abroad.

The temperature estimation method in the present embodiment includes a sampling step, a measurement step, and a calculation step.

FIG. 1 is a flowchart of the temperature estimation method in the present embodiment. Details of each step will be described below with reference to FIG. 1.

(Sampling Step)

In the sampling step, ester oil is sampled from the oil-immersed electric appliance.

In order to perform the temperature estimation method in the present embodiment, initially, ester oil is sampled from an oil drain valve of the oil-immersed electric appliance to a glass container or a polyethylene container. Since ester oil circulates through the inside of the electric appliance, a thermal decomposition product of ester oil is distributed in the appliance at a substantially uniform concentration. Though an amount of insulating oil actually used for analysis is approximately 0.1 mL, 10 mL to 100 mL of oil is preferably sampled in consideration of introduction of a foreign matter from the outside.

(Measurement Step)

In the measurement step, concentrations of two types of thermal decomposition products in ester oil sampled in the sampling step (compounds generated as a result of thermal decomposition of components in ester oil) are measured.

Measurement can be conducted, for example, with such an analysis instrument as a gas chromatograph mass spectrometer (GC/MS). The analysis method should only be able to analyze thermal decomposition products of ester oil, and another column, another analysis condition, or another analyzer adapted to a gas chromatograph or the like incorporating an FID detector may be employed.

Before the sampled ester oil is subjected to analysis, a standard solution in which each thermal decomposition product has been dissolved at an already known concentration is also subjected to measurement in advance, and based on a measurement value therefrom, a calibration curve is prepared. With the calibration curve, a concentration of a thermal decomposition product contained in the sampled ester oil can be calculated. In the present embodiment, two types of thermal decomposition products which are detected are fatty acids.

(Calculation Step)

In the calculation step, a temperature of the heat generating site in the oil-immersed electric appliance is calculated based on a concentration ratio between the two types of thermal decomposition products and a relational expression between the temperature of the heat generating site and the concentration ratio prepared in advance.

Initially, before the calculation step, Test Example 2 (a heating test) which will be described later is performed in advance and a relational expression between a temperature of the heat generating site and a concentration ratio (calibration curve) is prepared as in Examples.

Then, a concentration ratio is calculated based on measurement values of concentrations of the two types of thermal decomposition products. A temperature of the heat generating site in the oil-immersed electric appliance can be calculated from the concentration ratio based on the relational expression between the temperature of the heat generating site and the concentration ratio prepared in advance.

A concentration ratio serving as an indicator for estimation of a temperature is preferably a concentration ratio of branched fatty acid/straight-chain fatty acid, straight-chain fatty acid/branched fatty acid, saturated fatty acid/unsaturated fatty acid, or unsaturated fatty acid/saturated fatty acid, and more preferably a concentration ratio of straight-chain fatty acid/branched fatty acid.

It has been confirmed in the studies conducted by the present inventors that these concentration ratios highly correlate with a temperature of the heat generating site in a wide temperature range (in particular, in a high-temperature region) (see Examples). A temperature of the heat generating site in the oil-immersed electric appliance immersed in ester oil can highly accurately be estimated by using these concentration ratios.

In the measurement step, two types of thermal decomposition products corresponding to these combinations of concentration ratios are subjected to measurement.

A concentration of a thermal decomposition product generated as a result of occurrence of abnormal overheat in the oil-immersed electric appliance is different depending on a duration of abnormal overheat and an area (a volume) of the heat generating site other than the temperature of the heat generating site, and it is difficult to estimate a temperature of the heat generating site (a temperature of abnormal overheat) with only a concentration of a thermal decomposition product being used as the indicator.

A concentration ratio between two types of thermal decomposition products in ester oil, however, is dependent on a temperature of the heat generating site, not on a duration of abnormal overheat or an area of the heat generating site. Since an amount of insulating oil (ester oil) is sufficiently greater than an amount of generation of a thermal decomposition product and close to indefinite supply, the thermal decomposition product is kept generated at a constant rate at a certain temperature and a concentration ratio between two types of thermal decomposition products is constant. Therefore, the concentration ratio between two types of thermal decomposition products can be considered as dependent only on a temperature, not on time or an area. This is considered as similarly applicable also to analysis of gas components in insulating oil in maintenance of an oil-immersed transformer (see Electric Technology Research Association, "Denki Kyodo Kenkyu," Vol. 54, No. 5 (1), page 33, right column, lowermost paragraph, section (katakana character "i")).

Therefore, a temperature of abnormal overheat can be estimated by using a concentration ratio between two types of thermal decomposition products in the present embodiment.

Though a method with the use of two types of thermal decomposition products as the indicator is described in the present embodiment, yet another indicator may also be added for estimation of a temperature of the heat generating site for the purpose of improving estimation accuracy.

When an estimated temperature value obtained with the temperature estimation method exceeds a statistically or empirically predetermined threshold temperature, measures for preventing occurrence of an internal abnormal condition can be taken by stopping an operation of the oil-immersed electric appliance. By thus using the temperature estimation method in the present embodiment, an internal abnormal condition (a failure) of an oil-immersed electric appliance can be predicted and precautionary maintenance of the oil-immersed electric appliance can be done.

In the present embodiment, an internal abnormal condition of an oil-immersed electric appliance can be predicted and precautionary maintenance of the oil-immersed electric appliance can be done without turning off the appliance for internal inspection each time of periodic check.

Test Example 2

In Test Example 2, concentrations of a plurality of thermal decomposition products at each temperature were measured in the test system (see FIG. 12) which simulated occurrence of abnormal overheat in an oil-immersed electric appliance immersed in ester oil. Relation between a concentration ratio between two thermal decomposition products and a heating temperature was analyzed based on measurement values in Examples and Comparative Examples which will be described later.

Thermal decomposition products subjected to measurement were heptanoic acid, octanoic acid, and decanoic acid representing straight-chain fatty acid and 2-ethylhexanoic acid representing branched fatty acid.

Referring to FIG. 12, in order to simulate occurrence of abnormal overheat in an oil-immersed electric appliance immersed in ester oil, a heat generating site or a heater 31 was set in test vessel 21 and ester oil 1 was heated, Synthetic ester oil was employed as ester oil 1. Test vessel 21 was provided with conservator 22 and heater 31 was powered by AC power supply 32.

Temperatures of heater 31 and ester oil 1 were measured with thermometer 41 and thermometer 42, respectively. Heating by heater 31 was controlled based on measurement values from thermometers 41 and 42, and a temperature of heater 31 was maintained at 300° C., 400° C., 500° C., 600° C., 700° C., 800° C., and 900° C. In order to uniformly dissolve a thermal decomposition product of the ester oil, ester oil 1 was agitated with agitator 5. After heating for ten minutes at each temperature, ester oil 1 was sampled with removable oil sampling syringe 6. Ester oil 1 (new oil) before heating was also sampled in advance as a control.

Concentrations of the four types of thermal decomposition products contained in the sampled ester oil were measured with a gas chromatograph mass spectrometer (GC/MS). Measurement was conducted three times for each ester oil sampled as above.

Specifically, 0.1 mL of sampled ester oil was dissolved in 1 mL of hexane, and the solution was directly introduced into the gas chromatograph mass spectrometer with a split method (at a split ratio of 1:10) and analyzed with an HP-5 column (having a length of 30 m×an inner diameter of 0.25 mm×a film thickness of 0.25 μm) of Agilent Technologies.

A temperature at an introduction port was raised in a procedure of "280° C., a column temperature being 60° C. (held for five minutes)"→"temperature increase (5° C./minute)"→"highest temperature at 300° C. (held for five minutes)."

A gas chromatograph mass spectrometer was used for identifying an unknown thermal decomposition product. After the thermal decomposition product was known, analysis could also be conducted with an analyzer capable of quantitatively analyzing that compound (for example, a gas chromatograph apparatus incorporating a hydrogen flame ionization detector (FID)).

When standard solutions in which various types of thermal decomposition products had been dissolved in ester oil at already known concentrations were also subjected to measurement and calibration curves were prepared at the same time, a concentration of a thermal decomposition product contained in the heated ester oil could be calculated based on the calibration curves.

Figure 13:
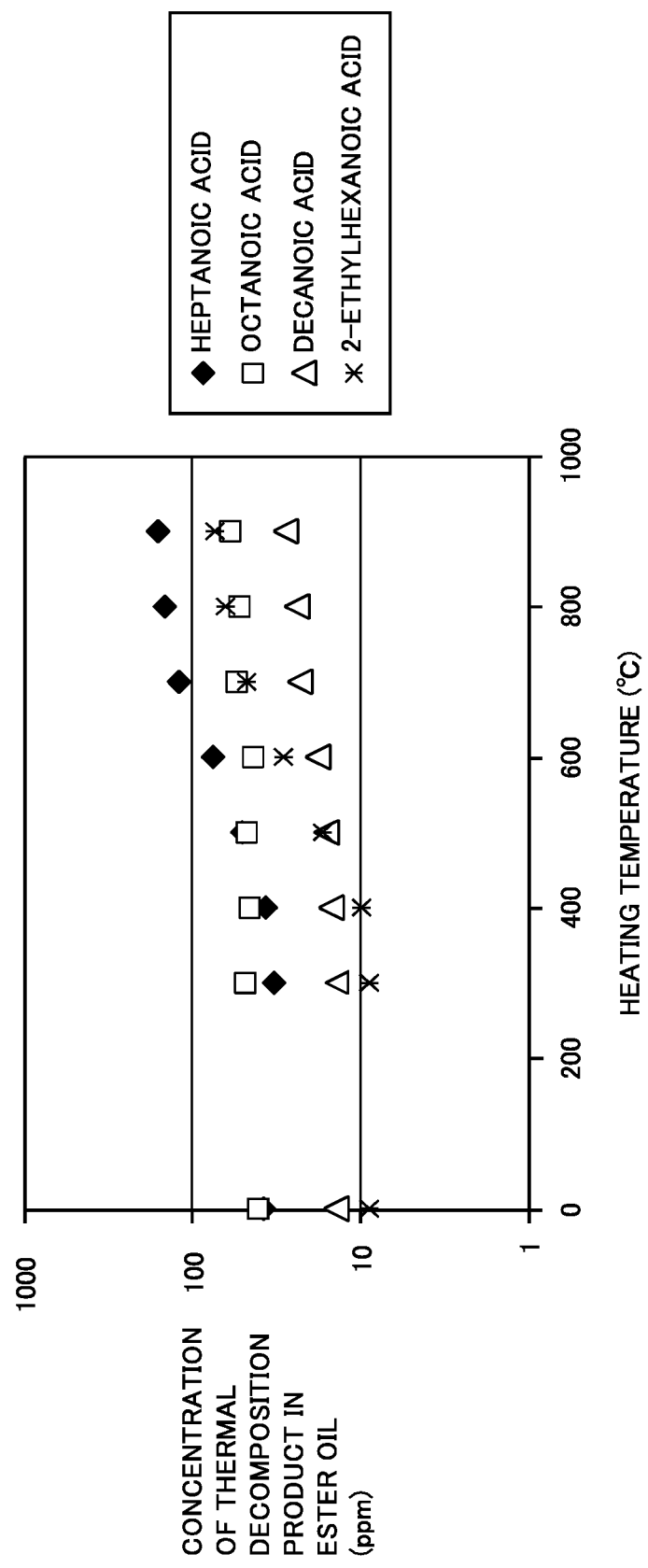
FIG. 13 shows a graph showing results of measurement of a concentration of a thermal decomposition product in Test Example 2.

Table 2 and FIG. 13 show results of measurement of a concentration of each thermal decomposition product at each heating temperature. FIG. 13 shows results of measurement of new oil in a portion where a heating temperature was 0.

TABLE 2

| | | Concentration of Thermal Decomposition Product (unit: ppm) | | | |
|---|---|---|---|---|---|
| | | Heptanoic Acid | Octanoic Acid | Decanoic Acid | 2-Ethyl-hexanoic Acid |
| Heating Temperature | New Oil | 38 | 41 | 14 | 9 |
| | 300° C. | 33 | 49 | 14 | 9 |
| | 400° C. | 37 | 46 | 15 | 10 |
| | 500° C. | 51 | 48 | 16 | 17 |
| | 600° C. | 76 | 44 | 18 | 29 |
| | 700° C. | 121 | 55 | 23 | 48 |
| | 800° C. | 147 | 53 | 24 | 64 |
| | 900° C. | 161 | 60 | 28 | 74 |

As shown in Table 2 and FIG. 13, a concentration in oil increases as a heating temperature is higher in all of the four types of fatty acids subjected to measurement.

As described above, in order to estimate a temperature of the heat generating site in the oil-immersed electric appliance immersed in ester oil, a concentration ratio between two types of thermal decomposition products is effectively used as the indicator. In Comparative Examples and Examples which will be described next, measurement results in Table 2 were used to calculate concentration ratios between two types of thermal decomposition products in various combinations and to analyze relation between the concentration ratio and a heating temperature.

Example 8

Figure 14:
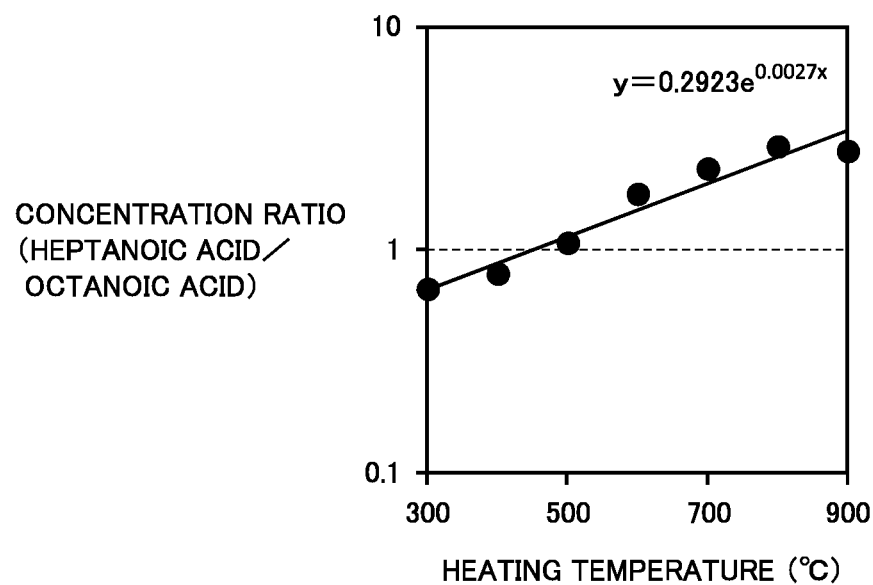
FIG. 14 shows a graph showing relation between a concentration ratio between thermal decomposition products (heptanoic acid/octanoic acid) and a heating temperature in Example 8.

FIG. 14 shows a graph showing relation between a concentration ratio between thermal decomposition products (heptanoic acid/octanoic acid) and a heating temperature in Example 8.

The figure shows a plot of a concentration ratio at each heating temperature, a regression line found from the plots with the least square method, and a relational expression (a regression expression) thereof, which is also applicable to a figure that follows.

The relational expression (calibration curve) was prepared not by using a temperature of ester oil but by using a heating temperature representing a temperature of heater 31 (a value measured with thermometer 41) which simulated a heat generating site. A temperature of the heat generating site in the oil-immersed electric appliance can thus be estimated based on the prepared calibration curve.

Even though heat generation such as abnormal overheat occurs in a part (a local part) of an oil-immersed electric appliance such as an actual transformer, a temperature of the insulating oil (ester oil 1) itself hardly increases from a temperature in a normal operation (around 100° C.).

In FIG. 14, heptanoic acid/octanoic acid highly correlated with a heating temperature in a temperature region from 300° C. to 900° C.

Example 9

Figure 15:
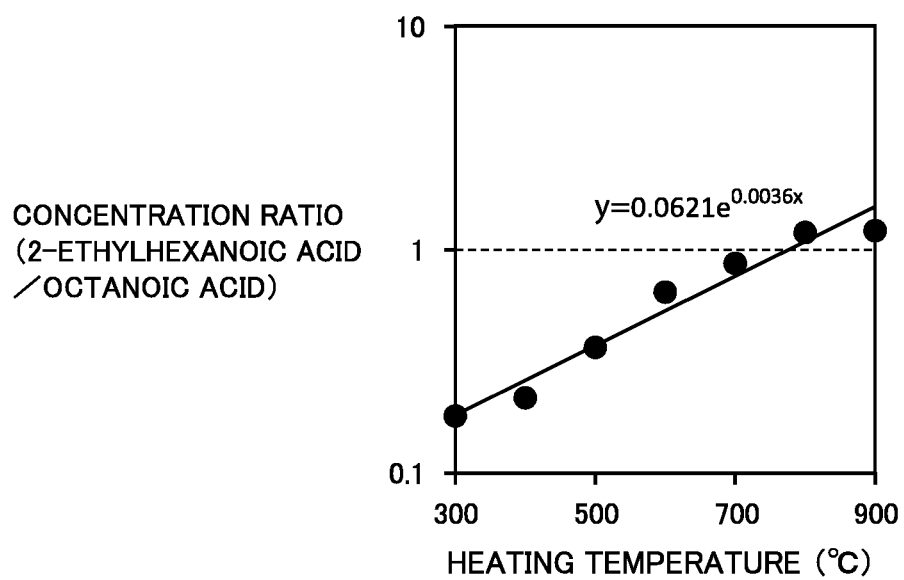
FIG. 15 shows a graph showing relation between a concentration ratio between thermal decomposition products (2-ethylhexanoic acid/octanoic acid) and a heating temperature in Example 9.

FIG. 15 shows a graph showing relation between a concentration ratio between thermal decomposition products (2-ethylhexanoic acid/octanoic acid) and a heating temperature in Example 9. As shown in FIG. 15, correlation also of the concentration ratio calculated in the combination with a heating temperature could be confirmed.

Approximation formulae in FIGS. 14 and 15 are now compared with each other. Consequently, the approximation formula ($y=0.2923e^{0.0027x}$) of the concentration ratio of heptanoic acid/octanoic acid was smaller in inclination than the approximation formula ($y=0.0621e^{0.0036x}$) of the concentration ratio of 2-ethylhexanoic acid/octanoic acid. It is thus considered that reliability of an estimated temperature is higher in estimating an overheat temperature with the concentration ratio of branched fatty acid/straight-chain fatty acid than estimating an overheat temperature with the concentration ratio of straight-chain fatty acid/straight-chain fatty acid. It is thus considered that reliability of the estimated temperature is higher by calculating a concentration ratio by using fatty acids different in structure. Therefore, it is considered that reliability of an estimated temperature is high also when a heating temperature is estimated with concentration ratios of straight-chain fatty acid/branched fatty acid, unsaturated fatty acid/saturated fatty acid, and saturated fatty acid/unsaturated fatty acid.

It should be understood that the embodiments disclosed herein are illustrative and non-restrictive in every respect. The scope of the present invention is defined by the terms of the claims rather than the description above and is intended to include any modifications within the scope and meaning equivalent to the terms of the claims.

REFERENCE SIGNS LIST

1 insulating oil (silicone oil or ester oil); 21 test vessel; 22 conservator; 31 heater; 32 AC power supply; 41, 42 thermometer; 5 agitator; and 6 oil taking syringe

The invention claimed is:

1. A temperature estimation method of estimating a temperature of a heat generating site in an oil-immersed electric appliance immersed in insulating oil, the insulating oil being silicone oil or ester oil, the temperature estimation method comprising:
   a measurement step of measuring concentrations of two types of thermal decomposition products in the insulating oil; and
   a calculation step of calculating a temperature of the heat generating site in the oil-immersed electric appliance based on a concentration ratio between the two types of thermal decomposition products and a relational expression between the temperature of the heat generating site and a reference concentration ratio prepared in advance,
   at least one of the two types of thermal decomposition products being straight-chain siloxane, alcohol containing silicon, or benzene when the silicone oil is adopted as the insulating oil, and
   the two types of thermal decomposition products being fatty acids when the ester oil is adopted as the insulating oil.

2. The temperature estimation method according to claim 1, wherein
   the concentration ratio is a concentration ratio of branched fatty acid/straight-chain fatty acid, straight-chain fatty acid/branched fatty acid, saturated fatty acid/unsaturated fatty acid, or unsaturated fatty acid/saturated fatty acid when the ester oil is adopted as the insulating oil.

3. The temperature estimation method according to claim 1, wherein
   the straight-chain siloxane is hexamethyldisiloxane or octamethyltrisiloxane.

4. The temperature estimation method according to claim 3, wherein
   the alcohol containing silicon is trimethylsilanol.

5. The temperature estimation method according to claim 3, wherein
   the concentration ratio is a concentration ratio of hexamethylcyclotrisiloxane/trimethylsilanol, benzene/hexamethylcyclotrisiloxane, octamethylcyclotetrasiloxane/trimethylsilanol, benzene/octamethylcyclotetrasiloxane, octamethyltrisiloxane/hexamethyldisiloxane, or benzene/trimethylsilanol when the silicone oil is adopted as the insulating oil.

6. The temperature estimation method according to claim 3, wherein
   the concentration ratio is a concentration ratio of branched fatty acid/straight-chain fatty acid, straight-chain fatty acid/branched fatty acid, saturated fatty acid/unsaturated fatty acid, or unsaturated fatty acid/saturated fatty acid when the ester oil is adopted as the insulating oil.

7. The temperature estimation method according to claim 1, wherein
   the alcohol containing silicon is trimethylsilanol.

8. The temperature estimation method according to claim 7, wherein
   the concentration ratio is a concentration ratio of hexamethylcyclotrisiloxane/trimethylsilanol, benzene/hexamethylcyclotrisiloxane, octamethylcyclotetrasiloxane/trimethylsilanol, benzene/octamethylcyclotetrasiloxane, octamethyltrisiloxane/hexamethyldisiloxane, or benzene/trimethylsilanol when the silicone oil is adopted as the insulating oil.

9. The temperature estimation method according to claim 7, wherein
   the concentration ratio is a concentration ratio of branched fatty acid/straight-chain fatty acid, straight-chain fatty acid/branched fatty acid, saturated fatty acid/unsaturated fatty acid, or unsaturated fatty acid/saturated fatty acid when the ester oil is adopted as the insulating oil.

10. The temperature estimation method according to claim 1, wherein
    the concentration ratio is a concentration ratio of hexamethylcyclotrisiloxane/trimethylsilanol, benzene/hexamethylcyclotrisiloxane, octamethylcyclotetrasiloxane/trimethylsilanol, benzene/octamethylcyclotetrasiloxane, octamethyltrisiloxane/hexamethyldisiloxane, or benzene/trimethylsilanol when the silicone oil is adopted as the insulating oil.

11. The temperature estimation method according to claim 10, wherein
    the concentration ratio is a concentration ratio of branched fatty acid/straight-chain fatty acid, straight-chain fatty acid/branched fatty acid, saturated fatty acid/unsaturated fatty acid, or unsaturated fatty acid/saturated fatty acid when the ester oil is adopted as the insulating oil.

* * * * *